(12) United States Patent
Foss et al.

(10) Patent No.: US 6,559,158 B1
(45) Date of Patent: *May 6, 2003

(54) USE OF METHYLNALTREXONE AND RELATED COMPOUNDS TO TREAT CHRONIC OPIOID USE SIDE AFFECTS

(75) Inventors: Joseph F. Foss; Michael F. Roizen; Jonathan Moss; Chun-Su Yuan, all of Chicago, IL (US); William Drell, San Diego, CA (US)

(73) Assignees: UR Labs, Inc., Reno, NV (US); The University of Chicago, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/669,358

(22) Filed: Sep. 26, 2000

Related U.S. Application Data

(63) Continuation-in-part of application No. 09/120,703, filed on Jul. 22, 1998, which is a continuation-in-part of application No. 08/962,742, filed on Nov. 3, 1997, now Pat. No. 5,972,954, said application No. 09/669,358.
(60) Provisional application No. 60/168,480, filed on Dec. 1, 1999.

(51) Int. Cl.$^7$ ............................................. A61K 31/485
(52) U.S. Cl. ....................................................... 514/282
(58) Field of Search ........................................ 514/282

(56) References Cited

U.S. PATENT DOCUMENTS

| | | | |
|---|---|---|---|
| 4,176,186 A | 11/1979 | Goldberg et al. | 424/260 |
| 4,311,833 A | 1/1982 | Namikoshi et al. | 536/90 |
| 4,377,568 A | 3/1983 | Chopra | 424/31 |
| 4,385,078 A | 5/1983 | Onda et al. | 427/3 |
| 4,457,907 A | 7/1984 | Porter | 424/7.1 |
| 4,462,839 A | 7/1984 | McGinley et al. | 106/198 |
| 4,518,433 A | 5/1985 | McGinley et al. | 106/180 |
| 4,556,552 A | 12/1985 | Porter et al. | 424/32 |
| 4,606,909 A | 8/1986 | Bechgaard et al. | 424/21 |
| 4,615,885 A | 10/1986 | Nakagame et al. | 424/94 |
| 4,670,287 A | 6/1987 | Tsuji | 427/3 |
| 4,987,136 A | 1/1991 | Kreek et al. | 514/282 |
| 5,536,507 A | 7/1996 | Abramowitz et al. | 424/479 |
| 5,567,423 A | 10/1996 | Ying | 424/94.3 |
| 5,591,433 A | 1/1997 | Michael et al. | 424/184.1 |
| 5,597,564 A | 1/1997 | Ying | 424/94.65 |
| 5,609,871 A | 3/1997 | Michael et al. | 424/184.1 |
| 5,614,222 A | 3/1997 | Kaplan | 424/489 |
| 5,626,875 A | 5/1997 | Ballester Rodes et al. | 424/464 |
| 5,629,001 A | 5/1997 | Michael et al. | 424/234.1 |
| 5,811,451 A | 9/1998 | Minoia et al. | 514/443 |
| 5,866,164 A | 2/1999 | Kuczynski et al. | 424/472 |

FOREIGN PATENT DOCUMENTS

| | | |
|---|---|---|
| WO | WO97/33566 | 9/1997 |
| WO | WO98/25613 | 6/1998 |

OTHER PUBLICATIONS

Yuan, Chun Su et al., *European Journal of Pharmacology*, 276:107–111, 1995.
Yuan, Chun Su et al., *Clinical Pharmacology & Therapeutics*, 61:467–75, 1997.
Foss, Joseph F., *The Journal of Clinical Pharmacology*, 1997;37:25–30.
Yuan, Chun Su et al., *Clinical Pharmacology & Therapeutics*, 59:469–75, 1996.
Murphy et al., "Opioid–induced Delay in Gastric Emptying," *Anesthesiology*, vol. 87, No. 4 (Oct. 1997) pp. 765–770.
SKYES, Oral naloxone in opioid–associated constipation, *The Lancet* (1991), 337, 1475.
Yuan, Chun Su et al., *European Journal of Pharmacology*, 276:107–111, 1995.
Yuan, Chun Su et al., *Clinical Pharmacology & Therapeutics*, 61:467–75, 1997.
Foss, Joseph F., *The Journal Of Clinical Pharmacology*, 1997;37:25–30.
Yuan, Chun Su et al., *Clinical Pharmacology & Therapeutics*, 59:469–75, 1996.
Murphy et al., "Opioid–induced Delay in Gastric Emptying," *Anesthesiology*, vol. 87, No. 4 (Oct. 1997) pp. 765–770.

*Primary Examiner*—Phyllis G. Spivack
(74) *Attorney, Agent, or Firm*—Wolf, Greenfield & Sacks, P.C.

(57) ABSTRACT

A method of preventing or treating an opioid-induced side effect in a patient who has been chronically taking opioids, the method comprising administering a quaternary derivative of noroxymorphone in an amount sufficient to prevent or treat the side effect in the patient, but which amount would be insufficient to treat a patient with the same opioid-induced side effect who had not chronically been administered opioids.

43 Claims, 5 Drawing Sheets

US 6,559,158 B1

USE OF METHYLNALTREXONE AND RELATED COMPOUNDS TO TREAT CHRONIC OPIOID USE SIDE AFFECTS

CROSS-REFERENCE TO RELATED APPLICATION(S)

This application is a continuation-in-part of application Ser. No. 09/120,703, filed Jul. 22, 1998 (herein incorporated by reference); which is a continuation-in-part of application Ser. No. 08/962,742, filed Nov. 3, 1997, now patent Ser. No. 5,972,954, the disclosure of which is herein incorporated by reference. This application also claims priority of provisional Application No. 60/168,480, filed Dec. 1, 1999, also herein incorporated by reference.

STATEMENT REGARDING FEDERALLY SPONSORED RESEARCH OR DEVELOPMENT

Partial funding of the work described herein was provided under M01 RR00055 awarded by the U.S. Public Health Service General Clinical Research Center, and the U.S. Government has certain rights in the invention.

BACKGROUND OF THE INVENTION

The present invention is directed to the treatment of certain side effects associated with the use of opioids as analgesics. In particular, the present invention is directed to treating opioid-induced inhibition of gastrointestinal motility and constipation in patients chronically administered opioids.

Opioids are effective analgesics. However, their use is associated with a number of undesirable side effects, particularly when use is prolonged or chronic. Such side effects include pruritus, dysphoria, urinary retention, and inhibition of gastrointestinal motility. Opioids are widely used long-term to treat pain in advanced cancer patients, or patients in methadone maintenance treatment programs, for example. Opioid-induced changes in gastrointestinal motility are almost universal when these drugs are used long term, and there is no evidence of gastrointestinal compensation mechanisms. Constipation is the most common chronic side effect of opioid pain medications in patients with metastatic malignancy, and can be severe enough to limit opioid use or dose. Common treatments of bulking agents and laxatives have limited efficacy and may be associated with adverse side effects such as electrolyte imbalances. The significant negative impact on the quality of life of these patients has received insufficient attention in the past from the medical community in general, and from the oncology community in particular.

One treatment that has been used for opioid side effects is the use of opioid antagonists which cross the blood-brain-barrier, or which are administered directly into the central nervous system. Opioid antagonists such as naltrexone and naloxone have been administered intramuscularly or orally to treat opioid induced side effects. Naltrexone and naloxone are highly lipid soluble and rapidly diffuse across biological membranes, including the blood-brain barrier. Therefore, although naltrexone, naloxone, nalmefene, and other opioid antagonists may reverse many opioid side effects, because they diffuse into the central nervous system they have a narrow therapeutic window before they are observed to reverse the desired analgesic effect of the opioid being used. Additionally, in methadone maintenance patients, these tertiary compounds may also induce opioid withdrawal symptoms.

Many quaternary amine opioid antagonist derivatives do not reduce the analgesic effect of opioids. These quaternary amine opioid antagonist derivatives, which have a relatively higher polarity and reduced lipid solubility when compared to the tertiary forms of the drugs, were specifically developed to not traverse the blood-brain barrier or to traverse it at a greatly reduced rate. Methylnaltrexone (MNTX) is a quaternary ammonium opioid receptor antagonist that does not cross the blood-brain barrier in humans (see, e.g., U.S. Pat. No. 4,176,186, herein incorporated by reference). It offers the therapeutic potential to reverse undesired side effects of opioid pain medications mediated by peripherally located receptors (e.g., in the gastrointestinal tract) while sparing opioid effects mediated by receptors in the central nervous system, most importantly, analgesia.

However, high levels of MNTX in the plasma can lead to undesirable side effects such as orthostatic hypotension. Furthermore, high doses of opioid derivatives such as the tertiary and quaternary derivatives discussed above can be expensive.

It is therefore clear that there is a need to enhance palliative care in terminal cancer patients and others. It is also clear that a method for the prevention of opioid-induced and inhibition of gut motility constipation which does not counteract the analgesic effects of the opioid, or risk increased levels of pain is needed. Ideally, such a treatment has few side effects and is economical because administration of small amounts is effective.

SUMMARY OF THE INVENTION

The methods of the invention address the particular needs of patients undergoing long-term or chronic opioid administration. The quaternary derivatives used in this group of patients relieve the side effects and intestinal immobility caused by opioid use at surprisingly low doses, enhancing the patient's quality of life, maintaining analgesic efficacy, reducing health risks associated with opioid side effects, and reducing possible quaternary derivative side effects and costs.

"Long-term" opioid use or administration is intended to mean periods over about one week, and "chronic" use would generally mean a longer period.

The methods comprise administering a quaternary derivative of noroxymorphone intravenously in an amount such that peak plasma concentrations of the quaternary derivative do not exceed 2000 ng/ml and are preferably much less. The invention also includes methods wherein the derivative is administered orally, and wherein the peak plasma concentrations do not exceed 500 ng/ml, more preferably 250 ng/ml, and most preferably 100 ng/ml. The invention also includes a method for treating constipation in chronic opioid maintenance patients, the method comprising orally administering a non-enterically coated quaternary derivative of noroxymorphone in an amount less than 40 mg/kg. Preferably, the derivative is administered in an amount such that peak plasma concentrations of the quaternary derivative do not exceed 2000 ng/ml. The invention also includes a method for treating constipation in chronic opioid maintenance patients, the method comprising administering a quaternary derivative of noroxymorphone non-orally at a dose of less than 0.3 mg/kg, preferably less than 0.2 mg/kg, and most preferably the dose is less than 0.1 mg/kg. Also included in the invention is a method of preventing or treating opioid-induced side effects, the method comprising administering the opioid concurrently with an enterically coated quaternary derivative of noroxymorphone, the quaternary derivative being administered orally. The invention also includes a method as above, wherein the opioid and the quaternary derivative of noroxymorphone are combined in an oral dose. Dosing may be done daily, every other day, or as needed to provide relief from occasional or persistent constipation.

DETAILED DESCRIPTION OF THE INVENTION

Figure 1:
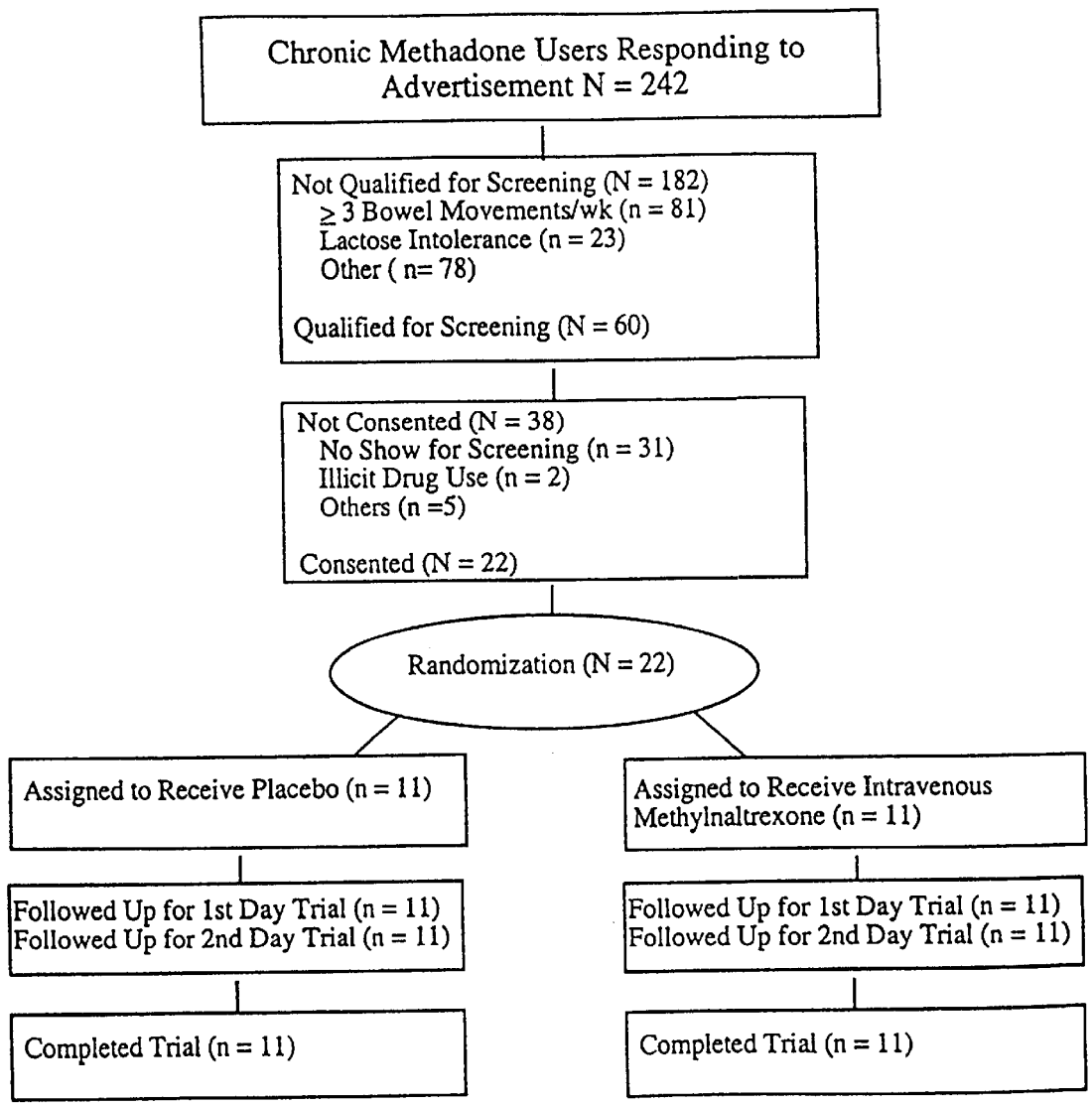
FIG. 1 is a flow diagram of participant screening, randomization and follow-up.

The present invention is directed to methods for preventing and treating the inhibition of gastrointestinal motility, particularly constipation, that arises in the group of patients taking chronic or maintenance doses of opioids. These patients include late stage cancer patients, elderly patients with osteoarthritic changes, methadone maintenance patients, neuropathic pain and chronic back pain patients. It has been discovered that the group of patients chronically taking opioids is surprisingly responsive to doses of quaternary derivatives of noroxymorphone that were previously considered too low to be clinically efficacious. Treatment of these patients is important from a quality of life standpoint, as well as to reduce complications arising from chronic constipation, such as hemorrhoids, appetite suppression, mucosal breakdown, sepsis, colon cancer risk, and myocardial infarction.

In the invention, a preferred quaternary derivative of noroxymorphone is methylnaltrexone. Preferred side effects to be treated include constipation and gastrointestinal motility inhibition, dysphoria, pruritus, and urinary retention.

When used as a treatment for these opioid-induced side effects, methylnaltrexone (MNTX) or other quaternary derivatives of noroxymorphone (QDMN) provide prolonged relief of the side effects. Idiopathic constipation, i.e., that due to causes other than exogenous administration of opioids, may be mediated by opioid sensitive mechanisms. Endogenous opioid receptors have been identified in the gut, and these receptors may modulate gut motility. Thus, administration of an opioid antagonist with peripheral action, such methylnaltrexone or other quaternary derivatives of noroxymorphone, would block the effects of endogenous opioids.

Quaternary derivatives of noroxymorphone are described in full in Goldberg et al., U.S. Pat. No. 4,176,186 (herein incorporated by reference), and in general are represented by the formula:

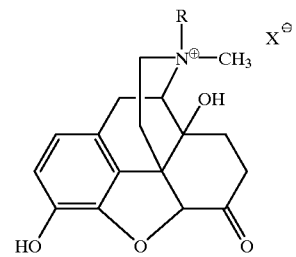

wherein R is allyl or a related radical such as chlorallyl, cyclopropyl-methyl or propargyl, and X is the anion of an acid, especially a chloride, bromide, iodide or methylsulfate anion.

The presently preferred quaternary derivative of noroxymorphone is methylnaltrexone. Methylnaltrexone is a quaternary amine derivative of naltrexone. Methylnaltrexone has been found to have only 2 to 4% of the opiate antagonistic activity of naltrexone in vivo due to its inability to pass the blood-brain-barrier and bind to the opiate receptors in the central nervous system.

Opioids are typically administered at a morphine equivalent dosage of: 0.005 to 0.15 mg/kg body weight for intrathecal administration; 0.05 to 1.0 mg/kg body weight for intravenous administration; 0.05 to 1.0 mg/kg body weight for intramuscular administration; 0.05 to 1.0 mg/kg body weight/hour for transmucosal or transdermal administration. By "morphine equivalent dosage" is meant representative doses of other opioids which equal one milligram of morphine, for example 10 mg meperidine, 1 mg methadone, and 80 μg fentanyl.

In accordance with the present invention, methylnaltrexone is administered at a dosage of: 0.001 to 1.0 mg/kg body weight for intravenous administration; 0.001 to 1.0 mg/kg body weight for intramuscular administration; 0.001 to 1.0 mg/kg body weight for transmucosal administration and 0.1 to 40.0 mg/kg body weight for oral administration.

The administration of the methylnaltrexone is preferably commenced prior to administration of the opioid to prevent opioid-induced side effects, including constipation. It is desirable to commence administration of methylnaltrexone about 5 minutes for parenteral MNTX administration and 20 minutes for enteral MNTX administration prior to administration of opioids in order to prevent these opioid-induced side effects. While the prevention of symptoms is preferred, in some patients, such as those chronically on opioids, prevention is not possible. However, methylnaltrexone administration may also be commenced after the administration of the opioid or after the onset of opioid induced symptoms as a treatment for those symptoms.

Methylnaltrexone is rapidly absorbed after oral administration from the stomach and bowel. Initial plasma levels of the drug are seen within 5–10 minutes of the administration of non-enteric coated compound. Addition of an enteric coating which prevents gastric absorption is associated with lower plasma levels of the methylnaltrexone.

For intravenous or intramuscular administration, methylnaltrexone (from, e.g., Mallinckrod Pharmaceuticals, St. Louis, Mo.) is formulated with saline or other physiologically acceptable carriers; for transmucosal administration the methylnaltrexone is formulated with a sugar and cellulose mix or other pharmacologically acceptable carriers known in the art; and for oral administration, the methylnaltrexone is provided in granules which can be coated or left uncoated, and can be put in gelatin capsules. An enteric coating manufactured by Coating Place, Inc., Verona, Wis. can be made as follows. The drug was prepared by encapsulating MNTX powder with a Eudragit L 100 and Myvacet 9–45 mixture. The final substance used in the study was the 45–80 mesh fraction which was 50% MNTX by weight. This was demonstrated to decrease release of the drug at gastric pH by 77% based on the methods of the USP/NF. These microencapsulated granules were then put into gelatin capsules for administration. Alternatively, methylnaltrexone is formulated with pharmacologically acceptable binders to make a tablet or capsule with or without an enteric coating. Methods for such formulations are well known to those skilled in the art (see e.g., *Remington: The Science and Practice of Pharmacy*, 19th ed. (1995) Mack Publishing Company, Easton, Pa.; herein incorporated by reference).

Any art-known transdermal application may be used, but transdermal administration is preferably via a patch applied to the skin with a membrane of sufficient permeability to allow diffusion of MNTX at a fixed rate in the range of 1.0 to 10.0 mg/hr. The rate of administration may be varied by varying the size of the membrane contact area and/or applying an electrical wiring potential to a drug reservoir. The patch preferably holds 25 mg to 1 gram of available drug in the reservoir plus additional drug as needed for the mechanics of the system.

In the description above and below, methylnaltrexone is used as an example of a particularly effective QDNM. It is apparent that other QDNMs may be used as desired, and appropriate dosage can readily be determined empirically by those of skill in the art to account for e.g., variable affinity of the QDNM for opiate receptors, different formulations, etc.

The following Examples are intended to illustrate aspects of the invention and are not to be construed as limitations upon it.

EXAMPLE 1

Effects of Standard MNTX Dosage on Chronic Opioid Patients

Subjects

With approval from the Institutional Review Board at the University of Chicago, two male and two non-pregnant female adults participating in a methadone maintenance program were enrolled in this study. All four subjects were African Americans. Their mean age ±SD (range) was 45.3±8.6 (35–56) years.

Subjects in this study met the following inclusion criteria: (1) They were currently enrolled in a methadone maintenance program for at least 1 month; (2) they experienced methadone-induced constipation, i.e. less than one bowel movement in the previous 3 days or less than three bowel movements in the previous week (O'Keefe et al., *J. Gerontol.*, 50:184–189 (1995); Parup et al., *Scand. J Gastroenterol*, 33:28–31 (1998)). Exclusion criteria were as follows: (1) History or current evidence of significant cardiovascular, respiratory, endocrine, renal, hepatic, hematological or psychiatric disease; (2) any laboratory findings indicating hepatic or renal impairment, or abnormal physical examination findings; (3) current use of other medications or evidence of illicit drug use; (4) known hypersensitivity to lactose or lactulose; (5) participation in any investigational new drug study in the previous 30 days; (6) subject is breastfeeding. Subjects also agreed not to take any laxatives for 2 days before the beginning of the study and during the study.

Protocol

After obtaining written, informed consent, subjects were admitted to the Clinical Research Center at the University of Chicago Medical Center for up to 8 days. Methylnaltrexone dose of 0.45 mg/kg was chosen to start this trial because this dose was previously given in normal volunteers and prevented opioid-induced delay of the oral-cecal transit time without any side effects (Yuan et al., *Clin. Pharmacol Ther.*, 59:469–475 (1996)). Drug administration was performed single blind to the subjects in this pilot study. Thus, methylnaltrexone dose could be adjusted based on subjects' clinical response during the study.

All four subjects received test drug (normal saline or methylnaltrexone (N-methylnaltrexone bromide, prepared by Mallinckrodt Specialty Chemicals, St. Louis, Mo.)) twice daily at 09:00 h and 21:00 h, except on the last day of the study in which they received test drug only at 09:00 h. All four subjects received placebo (normal saline) on Day 1. Thereafter, subjects received intravenous methylnaltrexone until the end of the study.

On Day 2 at 09:00 hours (h), Subjects 1 and 2 were given 0.45 mg/kg intravenous methylnaltrexone over 1 min. Subject 2 experienced severe abdominal cramps after receiving the compound and was withdrawn from the study. Subject 1 did not experience abdominal cramps after the first dose of methylnaltrexone, but was given placebo in place of the compound at the regularly scheduled dosing times for Day 2 and Day 3 to maintain the single blind study while the reaction of Subject 2 was investigated. Beginning on Day 4, the study was resumed for Subject 1 using 0.45 mg/kg of methylnaltrexone, diluted with 50 ml normal saline and administered over 30 min. Infusion could be stopped at any time for complaints of abdominal pain.

For Subjects 3 and 4, the study was shortened from 8 to 5 days, methylnaltrexone dosage was decreased, and a new, three-step dosing procedure was established. Methylnaltrexone 0.05 mg/kg, mixed in 30 ml normal saline (first syringe), was infused intravenously over 10 min. The subject was then observed 10 min for drug response. If there was no response, then methylnaltrexone 0.1 mg/kg (second syringe), mixed in 30 ml normal saline, was infused over 15 min. Subject was observed 15 min for drug response. If there was no response, then methylnaltrexone 0.3 mg/kg (third syringe), mixed in 30 ml normal saline, was infused over 15 min.

Vital signs were obtained at 0, 5, 10, 30, 60, 90 and 120 min after each test drug administration. For oral-cecal transit time measurement, 10 g lactulose (Solvay Pharmaceuticals, Marietta, Ga.) was administered orally at 09:00 h of Day 1, Day 5 and Day 8 for Subject 1; of Day 1 for Subject 2, and of Day 1, Day 3 and Day 5 for Subjects 3 and 4. Illicit drug use was monitored by random urine drug screens.

Blood and Urine Sampling and Analysis, Bowel function Assessment

After each test drug administration, seven blood samples (5 ml each) were obtained at time 0, 5, 30 min, and 1, 2, 4, 8 h, and three urine samples were collected at time 0, 2, and 4 h. Plasma and urine methylnaltrexone levels were determined by an HPLC technique with a detection limit of 2 ng/ml (Kim et al., 1989; Yuan et al., *Clin. Pharmacol Ther.*, 59:469–475 (1996); both herein incorporated by reference). Subjects were asked to record frequency and consistency of stools during the stud), period. Subjects' bowel movements were witnessed and recorded by a research nurse.

Oral-cecal Transit Time Measurement

The oral-cecal transit time was assessed by the pulmonary hydrogen ($H_2$) measurement technique, which measures pulmonary $H_2$ that is produced when unabsorbed lactulose is fermented by colonic bacteria and excreted in the breath. This $H_2$ production is reflected by a concomitant increase in breath $H_2$ excretion. The time between ingestion and the earliest detectable and sustained rise in pulmonary hydrogen excretion, i.e., a sudden rise to peak (>25 ppm), or an increase of at least 2 ppm above the baseline, maintained and increased in three consecutive samples, indicates that lactulose has reached the cecum and represents the oral-cecal transit time see e.g., Yuan, et al., *Clin. Pharmacol Ther.*, 59:469–475 (1996); Bond and Levitt, *J. Lab Clin. Med.*, 85:546–555 (1975); Read, et al., *Gut.*, 26:834–842 (1985); Basilisco, et al., *Dig. Dis. Sci.*, 32:829–832 (1987)). Hydrogen breath tests were conducted every 15 min until oral-cecal transit time was determined.

Evaluation Of Central Opioid Withdrawal

To evaluate possible opioid withdrawal with methylnaltrexone, subjects were asked to rate on a 5-point scale from 0 (not at all) to 4 (extremely) an objective checklist Withdrawal Scale (Fraser et al., *J Pharmacol Exp. Ther.*, 133:371–387 (1961); Jasinski, *Drug Addiction J.*, 197–258 (1977); both herein incorporated by reference). Items to be rated were: muscle cramps, flushing, painful joints, yawning, restless, watery eyes, runny nose, chills or gooseflesh, sick to stomach, sneezing, abdominal cramps, irritable, backache, tense and jittery, sweating, depressed/sad, sleepy, shaky (hands), hot or cold flashes, and bothered by noises. The ratings for individual items were summed for a total score for each scale. The total scores were compared before and after methylnaltrexone administration to see if there was a significant difference.

Results

All four subjects showed no response to placebo injection. Subjects 1 and 2, who received a methylnaltrexone dose of 0.45 mg/kg, showed immediate positive Taxation during or immediately after intravenous drug infusion. During 7 days of methylnaltrexone administration, Subject 1 did not experience any significant side effects, and reported mild abdominal cramping after each injection. Subject 2, however, had severe abdominal cramping after a single dose of methylnaltrexone, but showed no signs of systemic withdrawal such as lacrimation, diaphoresis, mydriasis, or hallucinations. Subject 2 was released without receiving additional methylnaltrexone.

Subjects 3 and 4 received intravenous methylnaltrexone (0.05–0.15 mg/kg) twice daily for 4 consecutive days. This 0.05–0.15 mg/kg dose range induced immediate laxation response in these two subjects, therefore, the third syringe injection (methylnaltrexone dose 0.3 mg/kg dose) was not administered during the study. No significant side effects were observed. Like Subject 1, both subjects described mild abdominal cramping, similar to a defecation sensation, without discomfort involved.

The stool frequency of these subjects increased from 1–2 times per week before the study to approximately 1.5 stool per day during the treatment period (Table 1). For Subjects 1, 3, and 4, oral-cecal transit times were reduced from 150, 150 and 150 min (after placebo) to 90, 60 and 60 min (after methylnaltrexone, at the end of the study), respectively. The baseline transit time for Subject 2 was 180 min. Due to the discontinuation of this subject, no other transit time was recorded after Day 1.

Peak plasma methylnaltrexone levels for Subjects 1, 2, 3 and 4 were 1.65, 1.10, 0.25 and 0.53 µg/ml, respectively.

TABLE 1

Intravenous methylnaltrexone reverses chronic-opioid induced gut motility and transit time changes in methadone subjects.

| Subject | Oral methadone (mg/day) | Intravenous methylnaltrexone (mg/kg) | Laxation response | Stool frequency Before study (per week) | Methylnaltrexone (per day) | Abdominal cramping | Central opioid withdrawal |
|---|---|---|---|---|---|---|---|
| #1 | 70 | 0.45, bid | Immediate | 1 | 1.5 | Mild | No |
| #2 | 38 | 0.45 | Immediate | 2 | 1 | Severe | No |
| #3 | 80 | 0.05–015, bid | Immediate | 2 | 1.3 | Mild | No |
| #4 | 65 | 0.05–0.15, bid | Immediate | 1.5 | 2 | Mild | No |

Discussion

In previous healthy volunteer studies, intravenous 0.45 mg/kg methylnaltrexone effectively prevented opioid-induced delay in oral-cecal transit time without affecting analgesia (Yuan et al., *Clin. Pharmacol Ther.*, 59:469–475 (1996)). However, that study was performed in normal volunteers after acute single administration doses of opioid and methylnaltrexone. Thus, the dose relationship of agonist to antagonist remained unknown in opioid-tolerant individuals, such as subjects in methadone maintenance programs as well as advanced cancer patients with chronic opioid pain medications.

When this study was designed, 0.45 mg/kg intravenous methylnaltrexone was chosen, the dose previously administered in normal volunteers that did not cause gastrointestinal symptoms (e.g. abdominal cramping) or laxation response. To achieve positive Taxation while limiting the possibility of adverse effects, BID dosing was planned for 7 days. Due to the fact that the elimination half-life of intravenous methylnaltrexone is approximately 2 h (Yuan et al., *Clin. Pharmacol Ther.*, 59:469–475 (1996); Foss et al., *J. Clin. Pharmacol*, 37:25–30 (1997)), no drug accumulation was expected in this study.

After intravenous injection, immediate bowel movements were observed in the first two subjects. While methylnaltrexone has been demonstrated to not reverse the analgesic effects of opioids (Yuan et al., *Clin. Pharmacol Ther.*, 59:469–475 (1996)), the potential effects of the compound in a population of chronic opioid users was unknown. Gastrointestinal symptoms are one of the hallmarks of gut withdrawal, and the persistent severe cramping in Subject 2, which required treatment, prompted a modification of the protocol. It is important to note, however, that none of the other primary indicators of opioid withdrawal were noted in this or any of the other subjects. For the next two subjects, the drug dose was reduced and the study duration shortened. While no effects were observed after placebo, positive laxation and significant reduction of the gut transit time were observed after a lower intravenous dose of methylnaltrexone in these two chronic methadone subjects.

Peak plasma levels of methylnaltrexone in all subjects were determined and were comparable to those seen in volunteers given similar doses (Yuan et al., *Clin. Pharmacol Ther.*, 59:469–475 (1996); Foss et al., *J. Clin. Pharmacol*, 37:25–30 (1997)). Subject 1, who had laxation but no other symptoms actually had higher peak plasma levels than Subject 2 (with the severe abdominal cramping), suggesting a difference in Subject 2's pharmacological response rather than a difference in pharmacokinetics.

The three subjects who completed the study reported mild abdominal cramping during intravenous methylnaltrexone infusion. The mild cramping appears to be a physiological desire to move the bowels, because the cramping disappeared after their bowel movement. Since the half-life of methylnaltrexone is approximately 2 h, one would expect that cramping caused by hyperactivity of the gut to be more prolonged. This indicates that methylnaltrexone and similar QDNMs are safe and ideal candidates to resolve opioid induced constipation without stimulant/laxative type side effects.

EXAMPLE 2

Effects of Variable MNTX Dosage on Chronic Opioid Patients

This Example was a double-blind, randomized, placebo-controlled trial, evaluating the effects of methylnaltrexone in treating chronic opioid-induced constipation. We conducted this trial using subjects in a methadone maintenance program, in,which approximately 60% of the chronic methadone users have constipation. These subjects served as a proxy group for advanced cancer patients to evaluate the efficacy of methylnaltrexone on chronic opioid-induced constipation.

With approval from the Institutional Review Board, 9 male and 13 non-pregnant, non-breastfeeding female adults were enrolled (FIG. 1). Their mean age±S.D. (range) was 43.2±5.5 (25–52) years. Subjects met the following inclusion criteria: (1) Enrollment in a methadone maintenance program for >1 month; (2) Methadone-induced constipation, i.e., 0–1 bowel movement in the previous three days, or 0–2 bowel movements in the previous week; (3) No laxative use two days before the study nor during the study. Exclusion criteria were as in the previous Example.

Protocol

An investigator explained the study procedures and obtained written, informed consent from 22 paid subjects. These subjects, who continued to receive their usual dose of methadone during the study, were admitted to the Clinical Research Center at the University of Chicago Medical Center for two days. An intravenous catheter was placed in each arm, one for test drug administration (placebo or methylnaltrexone [N-methylnaltrexone bromide], prepared by Mallinckrodt Specialty Chemicals, St. Louis, Mo.), and the other for blood drawing.

On Day 1, at 9 AM, after a restricted supper of no fiber the night before (required for the oral-cecal transit time measurement, see below) and overnight fasting, subjects were instructed to ingest 10 g lactulose (Solvay Pharmaceuticals, Marietta, Ga.) in 1.00 ml tap water. Subjects were also given placebo (normal saline) in four syringes (35 ml each) for intravenous injection (single-blinded to the subject).

On Day 1, at 5 PM, subjects were given placebo or methylnaltrexone up to 0.365 mg/kg over four syringes. Each syringe contained placebo or methylnaltrexone in 35 ml of normal saline, and was administered intravenously over nine minutes. For the methylnaltrexone group, syringes 1, 2, 3 and 4 contained 0.015, 0.05, 0.1 and 0.2 mg/kg study drug, respectively. The interval between administration of each syringe in both groups was one minute. The continued administration of each syringe depended on the absence of a clinical Taxation response (i.e., elimination of any stool) and/or potential side effects. Immediate Taxation was defined as defecation either during or within one minute after cessation of the infusion. The injection was discontinued if the subject had a bowel movement.

After a non-fiber supper the night before and overnight fasting, subjects on Day 2 at 9 AM, were again given test drug intravenously. Subjects were also given 10 g lactulose at this time. Day 2 studies were done to test the constancy of effect and to measure the oral-cecal transit time; this study did not have a crossover design.

Injection assignment was prepared using a table of random numbers from which sealed envelopes were prepared and opened sequentially as subjects were enrolled in the study. No stratification or blocking factors were used, except to insure that equal numbers of subjects were assigned to each treatment group after enrollment of the last ($22^{nd}$) subject. Randomization and test drug preparation were done by a biostatistician and a physician, respectively, who did not participate in data acquisition and evaluation.

Vital signs were obtained at 0, 5, 10, 30, 60, 90 and 120 min after each test drug administration. Illicit drug use was monitored by random urine drug screens.

Blood and Urine Sampling and Analysis

Blood and Urine Sampling and Analysis were Performed as in Example 1.

Bowel Function Assessment

Subjects were asked to record frequency and consistency of stools during the study period. Subjects' bowel movements were confirmed and recorded by a research nurse blinded to the group assignment. At the end of the study, the subjective opinion of each participant was gathered in order to rate subjects' satisfaction in respect to bowel movement.

Oral-cecal Transit Time Measurement

The oral-cecal transit time was assessed as in Example 1.

Evaluation of Central Opioid Withdrawal

To evaluate possible opioid withdrawal with methylnaltrexone, before and 10 min after the completion of test drug administration, subjects were asked to complete an objective checklist of withdrawal symptoms modified from Fraser et al. (*J. Pharmacol Exp. Ther.*, 133:371–387 (1961)) and Jasinski (*Drug Addiction J.*, 197–258 (1977)). Items rated (none, mild, moderate, severe) were yawning, lacrimation (excessive tearing), rhinorrhea (nasal discharge), perspiration, tremor, piloerection (goosebumps), and restlessness. The ratings for individual items were translated to a 0–3 scale and summed to give a total symptom score. The total scores before and after test drug administrations were compared between the groups. Potential opioid withdrawal symptoms were also monitored by an investigator throughout the study.

Statistical Analysis

Laxation responses were compared between groups using Fisher's exact test. The Mann-Whitney U test was used to compare the change from baseline in oral-cecal transit time between the two groups and to evaluate statistical differences between genders in oral-cecal transit times with P<0.05 considered statistically significant. Changes in opioid withdrawal symptoms were analyzed similarly.

Results

The mean stool frequency per week of the 22 subjects before the study was 1.5±0.7. All 22 subjects showed no response to placebo in the morning of Day 1. Eleven subjects were randomized to each treatment group. Those randomized to placebo received all four syringes in Day 1 afternoon and Day 2 morning sessions. As shown in Table 2, none of them showed any Taxation response after placebo, and no abdominal cramping was reported. At the end of the trial, seven of them were disappointed in respect to bowel movement satisfaction. There were no significant bowel movement frequency changes before and during the study. There were no opioid withdrawal and no significant side effects in these subjects.

Figure 2:
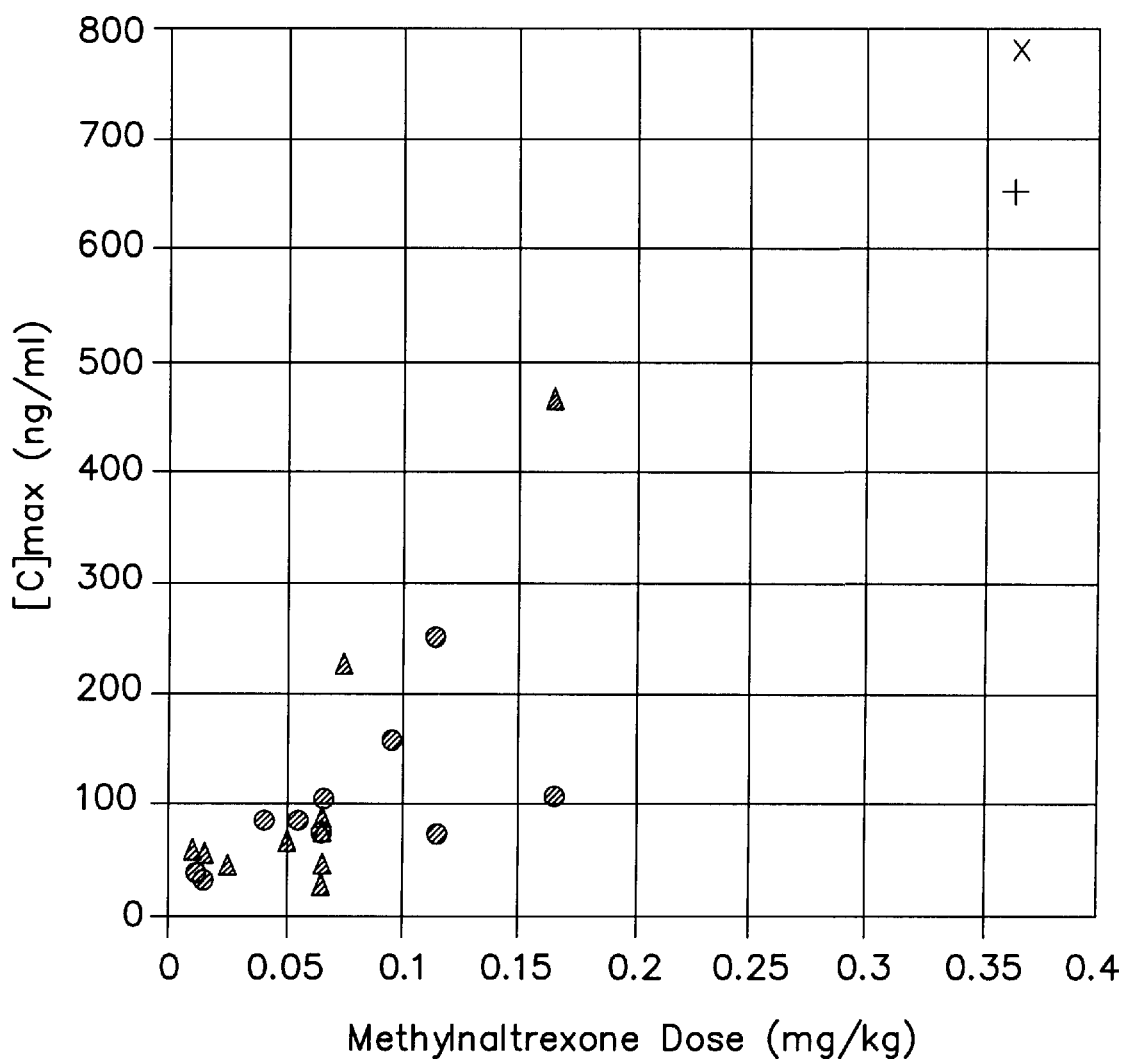
FIG. 2 shows a relationship between effective methylnaltrexone dose and peak plasma concentration in chronic methadone subjects. Peak plasma concentration ([C]max) is expressed as a function of methylnaltrexone dose that induced laxation response on first day administration (▲) and second day administration (●). Subject 13 failed to defecate at the maximum dose (0.365 mg/kg) on day one (×) but did respond to the same dose on day two (+). The $r^2$ value for the linear regression of concentration on effective dose is 0.77.

Ten subjects in the methylnaltrexone group had immediate Taxation response in the Day 1 afternoon session, and all 11 subjects had immediate Taxation in the Day 2 morning session (Fisher's exact P value<0.0001 when compared with placebo group response for both Days 1 and 2). The stool of most subjects (over 90%) was soft to loose and in large quantity. The methylnaltrexone dose received was 0.09±0.10 (0.01–0.37) mg/kg and 0.10±0.10 (0.01–0.37) mg/kg for Day 1 and Day 2, respectively. FIG. 2 shows the relationship between effective methylnaltrexone dose and peak plasma concentration.

During and immediately after each study drug injection, all subjects reported mild to moderate abdominal cramping, which they described as being similar to a defecation sensation, without discomfort involved. There was no opioid withdrawal symptoms observed in any of these subjects during the study. No significant side effects were reported by the subjects. Subject 13 reported mild light-headedness which resolved spontaneously. No subject demonstrated any clinically significant change in blood pressure or heart rate from baseline with either the placebo or study drug infusions. Subjects did not have additional bowel movements after drug-induced immediate Taxation, except Subject 15 who reported mild diarrhea. At the end of the study, all 11 subjects were satisfied with their bowel movement activity (Table 2).

TABLE 2

Methylnaltrexone (MNTX) reverses chronic opioid constipation in methadone subjects.

| Subject Number | Oral Methadone (mg/day) | Day One Test Drug (mg/kg) | Day One Laxation Response | Day Two Test Drug (mg/kg) | Day Two Laxation Response | Bowel movement Satisfaction |
|---|---|---|---|---|---|---|
| 1 | 50 | Placebo | No | Placebo | No | Disappointed |
| 2 | 65 | Placebo | No | Placebo | No | Disappointed |
| 4 | 85 | Placebo | No | Placebo | No | Disappointed |
| 5 | 61 | Placebo | No | Placebo | No | Disappointed |
| 8 | 42 | Placebo | No | Placebo | No | Disappointed |
| 11 | 89 | Placebo | No | Placebo | No | (not available) |
| 14 | 85 | Placebo | No | Placebo | No | Disappointed |
| 16 | 50 | Placebo | No | Placebo | No | Satisfied |
| 18 | 50 | Placebo | No | Placebo | No | Disappointed |
| 19 | 75 | Placebo | No | Placebo | No | (not available) |
| 22 | 50 | Placebo | No | Placebo | No | Somewhat satisfied |
| 3 | 55 | MNTX 0.015 | Immediate | MNTX 0.015 | Immediate | Very satisfied |
| 6 | 59 | MNTX 0.065 | Immediate | MNTX 0.065 | Immediate | Very satisfied |
| 7 | 68 | MNTX 0.165 | Immediate | MNTX 0.165 | Immediate | Very satisfied |
| 9 | 65 | MNTX 0.065 | Immediate | MNTX 0.115 | Immediate | Satisfied |
| 10 | 30 | MNTX 0.065 | Immediate | MNTX 0065 | Immediate | Very satisfied |
| 12 | 45 | MNTX 0.075 | Immediate | MNTX 0.115 | Immediate | Very satisfied |
| 13 | 100 | MNTX 0.365 | No | MNTX 0.365 | Immediate | Somewhat satisfied |
| 15 | 40 | MNTX 0.065 | Immediate | MNTX 0055 | Immediate | Very satisfied |
| 17 | 50 | MNTX 0.050 | Immediate | MNTX 0.095 | Immediate | Somewhat satisfied |
| 20 | 85 | MNTX 0.025 | Immediate | MNTX 0.040 | Immediate | Very satisfied |
| 21 | 75 | MNTX 0.011 | Immediate | MNTX 0.013 | Immediate | Very satisfied |

Figure 3:
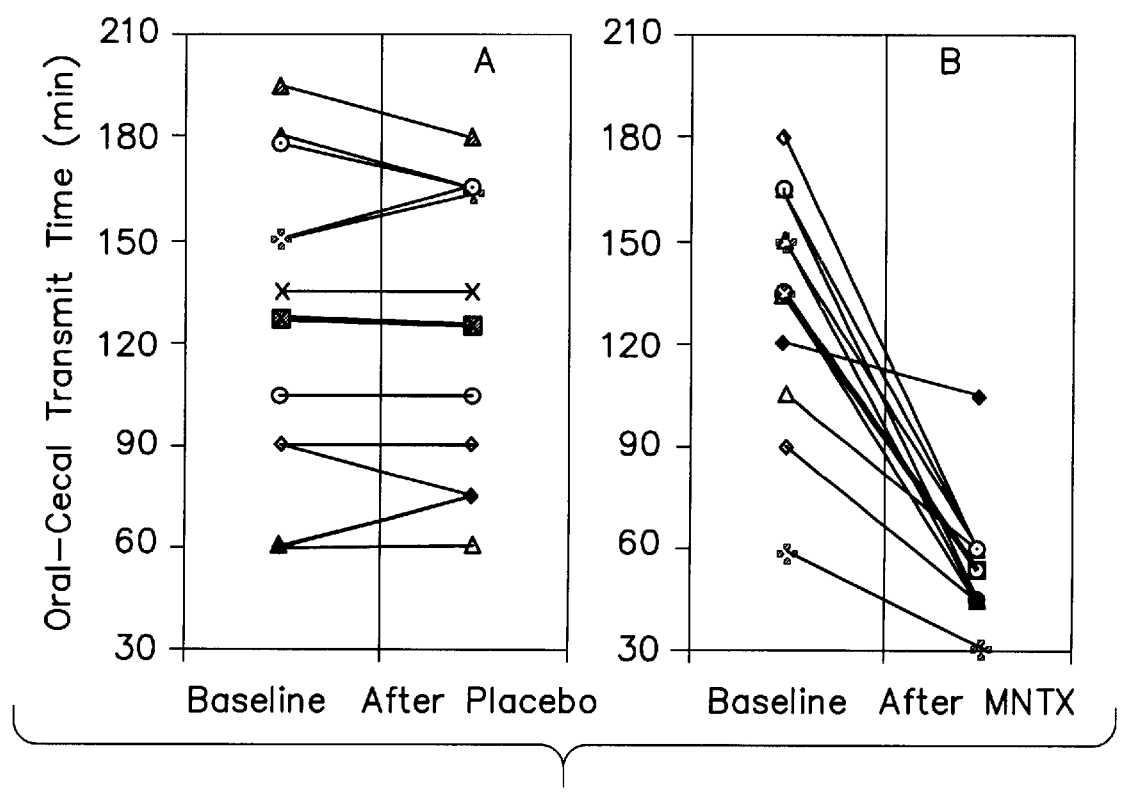
FIG. 3 shows changes in individual oral-cecal transit time of chronic methadone subjects. (A) The transit time (ordinate) of 11 subjects in placebo group from baseline to after placebo injection (abscissa). (B) The transit time (ordinate) of 11 methadone subjects in methylnaltrexone (MNTX) group from baseline to after study drug administration (abscissa). The heavy line represents the mean. The average change in the methylnaltrexone group was significantly greater than the average change in the placebo group (P<0.001).

Oral-cecal transit time data are presented in FIG. 3. The transit times for subjects in the placebo group (n=11) at baseline and after placebo injection were 126.8±48.3 (60–195) min and 125.3±45.0 (60–180) min, respectively. The transit times for subjects in the methylnaltrexone group (n=11) showed that the study drug reduced the transit time from the baseline level of 132.3±36.0 (60–180) min to 54.5±19.3 (30–105) min. The average chan the methylnaltrexone group (−77.7±37.2 min) was significantly greater than the average change in the placebo group (1.4±12.0 min) (P<0.001). There were no statistical differences in oral-cecal transit times between genders.

Peak plasma levels of 11 subjects in methylnaltrexone group for Day 1 and Day 2 were 162±237 (30–774) ng/ml and 166±177 (33–658) ng/ml, respectively. The percentage of intravenous dose excreted, unchanged in urine from 0 to 4 hr for Day 1 and Day 2 was 23.7±10.5 (9.6–39.9) % and 37.6±17.8 (13.2–73.6) %, respectively.

Discussion

The effect of opioids on gastrointestinal motility and transit is well appreciated as a clinical phenomenon. Opioids inhibit gastric emptying and propulsive motor activity of the intestine, thereby decreasing the rate of intestinal transit and producing constipation. It has been shown that opioid receptors and endorphins are widely distributed in the central nervous system and throughout the gastrointestinal tract.

Based on data obtained from previous animal experiments, the site of opioid action (central vs. peripheral) of exogenous opioid-induced gut motility change or constipation is still controversial (Daniel, et al., *Gastroenterology*, 36:510–523 (1959); Stewart, et al., *J. Pharmacol Exp. Ther.*, 205: 547–555 (1978); Tavani, et al., *Life Sci.*, 27:2211–2217 (1980); Galligan and Burks, *J. Pharmacol Exp. Ther.*, 226:356–361 (1983); Manara, et al., *J Pharmacol Exp. Ther.*, 237:945–949 (1986)). Since the translation of animal experiment data in the literature to humans is problematic due to differences in the physiology of the opioid systems, the action site for opioid-induced constipation in humans remains a matter of investigation. Methylnaltrexone, a peripheral opioid receptor antagonist, very effectively reversed chronic opioid constipation in this clinical trial. The data in these examples provide the first strong evidence that the methadone constipating effect in humans is predominantly mediated by receptors located in the peripheral gastrointestinal tract.

All 11 subjects who received intravenous methylnaltrexone had an immediate Taxation response, and all reported some degree (mild to moderate) of abdominal cramping prior to their bowel movement. We interpret their abdominal cramping as a physiological desire to defecate, because the cramping disappeared after their bowel movement. Because the half-life of methylnaltrexone is approximately two hours, one would expect that cramping caused by hyperactivity of the gut to be much more prolonged.

The lactulose hydrogen breath test was used, and subjects always received placebo the morning of Day 1 to establish an oral-cecal transit time baseline. Compared to baseline levels, we observed a significant reduction in gut transit time in all subjects after methylnaltrexone treatment. This result is consistent with the methylnaltrexone-induced clinical laxation response in these individuals. Lactulose, a non-absorbable osmotic agent that acts in the colon by increasing water content of the stool without directly stimulating gut peristaltic activity, may Rave laxative effects itself and could affect interpretation of our results. However, the dose used in this study (10 g) is ½ to ⅓ of a single dose and ⅙$^{th}$ to 1/12$^{th}$ the daily dose recommended to produce soft stools. This small dose of lactulose had no effect in our study, as indicated by the absence of a laxation response as well as no change in oral-cecal transit time in the placebo group.

A relatively wide dose range of intravenous methylnaltrexone was used to achieve clinical Taxation. In terms of individual subjects, however, the Taxation doses for Day 1 and Day 2 were very similar, and no tachyphylaxis was noticed. In this study, no opioid withdrawal symptoms were observed in our chronic methadone subjects, which further indicates that methylnaltrexone does not penetrate into the brain in humans. None of the 11 subjects in the methylnaltrexone group experienced significant side effects.

EXAMPLE 3

Effects of Oral Administration of MNTX on Chronic Opioid-Induced Constipation

Since oral medication is a safer and more convenient way to deliver drugs than is intravenous administration, the efficacy of oral MNTX in relieving constipation in methadone maintained patients was evaluated. Twelve constipated adults ($\leq 2$ stool/week) were enrolled. Their daily methadone dose was 73.3±16.2 mg (41–100 mg), mean±SD (range). On day 1 at 9AM, subjects ingested 10 g lactulose (Solvay Pharmaceuticals) to assess oral-cecal transit time as described above, and a placebo capsule. On day 2 at 9AM, subjects again received lactulose, and a capsule containing methylnaltrexone (Mallinckrodt). Ascending oral methylnaltrexone doses (0.3, 1.0, and 3,0 mg/kg) were given to 3 groups of 4 subjects per group. Drug administrations were single-blinded to the subject. Laxation response and potential opioid withdrawal were recorded and blood samples were collected.

Figure 4:
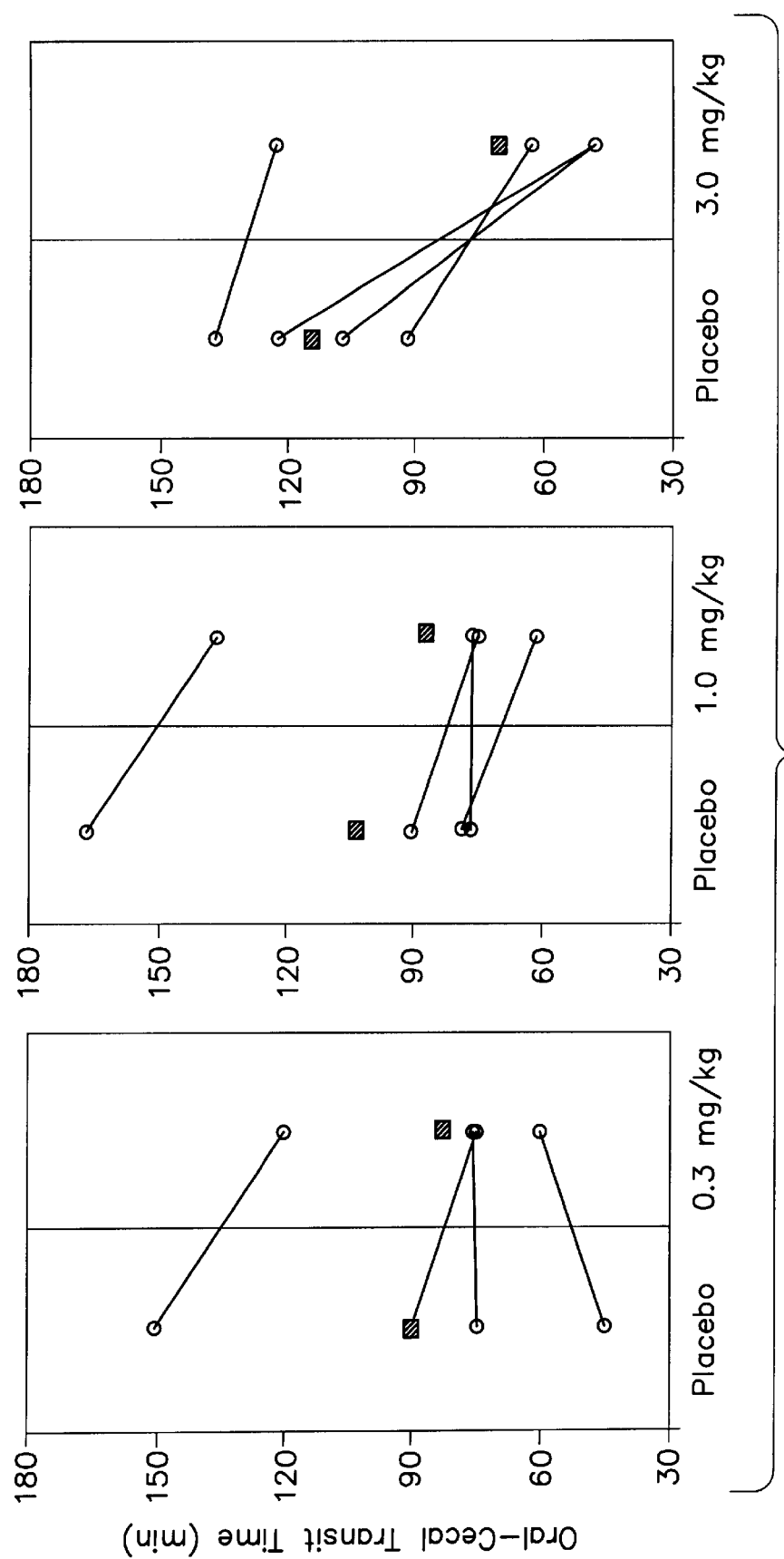
FIG. 4 shows changes in individual oral-cecal transit times (ordinate) of 12 chronic methadone subjects after placebo and three oral methylnaltrexone doses (4 subjects in each dose group). Filled squares represent mean values.

None of the 12 subjects showed Taxation response to placebo on day 1. On day 2, 3 out of 4 subjects had a bowel movement 18.0±8.7 hr (8–24 hr) after receiving 0.3 mg/kg MNTX. All subjects in the 1.0 mg/kg group and 3.0 mg/kg group had bowel movements at 12.3±8.7 hr (3–24 hr) and 5.2±4.5 hr (1.2–10 hr) after receiving oral compound, respectively. Most subjects reported very mild abdominal cramping after oral MNTX. Bowel movements, in most cases, were loose and in large quantity. There was no opioid withdrawal in any subjects, and no adverse effects were reported. Dose-related reduction of oral-cecal transit times is shown in FIG. 4. Oral MNTX has a significant dose-response effect ($p<0.05$) using the Spearman rank correlation coefficient test and linear regression model. Eight subjects had undetectable methylnaltrexone in their plasma. Peak plasma level for another 4 subjects (one from 1.0 mg/kg group and three from 3.0 mg/kg group) was 17.8±6.6 ng/ml (10–26 ng/ml).

EXAMPLE 4

Effects of MNTX on Patients Administered Opioids Non-Chronically

Subjects

With approval from the Institutional Review Board at the University of Chicago, seven men and seven nonpregnant women were enrolled in this double-blind, randomized placebo-controlled study. Mean age±SD was 25.8±8.4 years: age range was 18 to 43 years. Subjects were screened for drug abuse disorders or medical contraindications that would keep them from participating in the study.

Protocol

Subjects fasted from midnight the night before the study day and were admitted for each experimental day (or session) in the morning to the Clinical Research Center at the University of Chicago Medical Center. Sessions were separated by at least 1 week. Each session lasted approximately 7 hours, and the subjects received one of three injections: (1) placebo plus placebo, (2) placebo plus 0.05 mg/kg morphine, or (3) 0.45 mg/kg methylnaltrexone plus 0.05 mg/kg morphine. Injection I was given at the first session, and the subjects were blinded to the medication. Injections 2 and 3 were given in a random order, and the subjects and observers were blinded to the medication. Injection assignments were prepared by random selection on a computer and were sealed in envelopes. Drug preparation and administration was done by a physician who did not participate in subject observation and data acquisition.

After completion of the above three injections, we asked six of the subjects, beginning with those who had completed the study last, to return for a fourth injection (0.45 mg/kg methylnaltrexone plus 0.1 mg/kg morphine). This was done to evaluate the effects of methylnaltrexone with a higher does of morphine.

Drugs

The following drugs were used: morphine sulfate (Elkins-Sinn, Cherry Hill, N.J.), N-methylnaltrexone bromide (Mallinckrodt Specialty Chemicals, St. Louis, Mo.), and lactulose (Duphalac, Solvay Pharmaceuticals, Marietta, Ga.).

Statistics

Results of the hydrogen breath test after different injections were analyzed with the use of the Wilcoxon matched-pairs signed-rank test, with p<0.05 considered to be statistically significant. The Mann-Whitney U test was used to evaluate statistical differences between genders in oral-cecal transit times and in cold-indicted paid scores.

Results

Two female subjects were excluded from the study after the first (placebo plus placebo) session. One of them showed a relatively high and unstable baseline $H_2$ peak value (12 ppm) 2 hours after drinking lactulose. $H_2$ production requires a colonic bacterial flora capable of fermenting carbohydrate and yielding $H_2$. In in vivo studies of humans who had ingested lactulose and in vitro studies of fecal incubates with varying carbohydrates, $H_2$ was not produced in 2% to 27% of individuals tested.

Oral-cecal Transit Time

Figure 5:
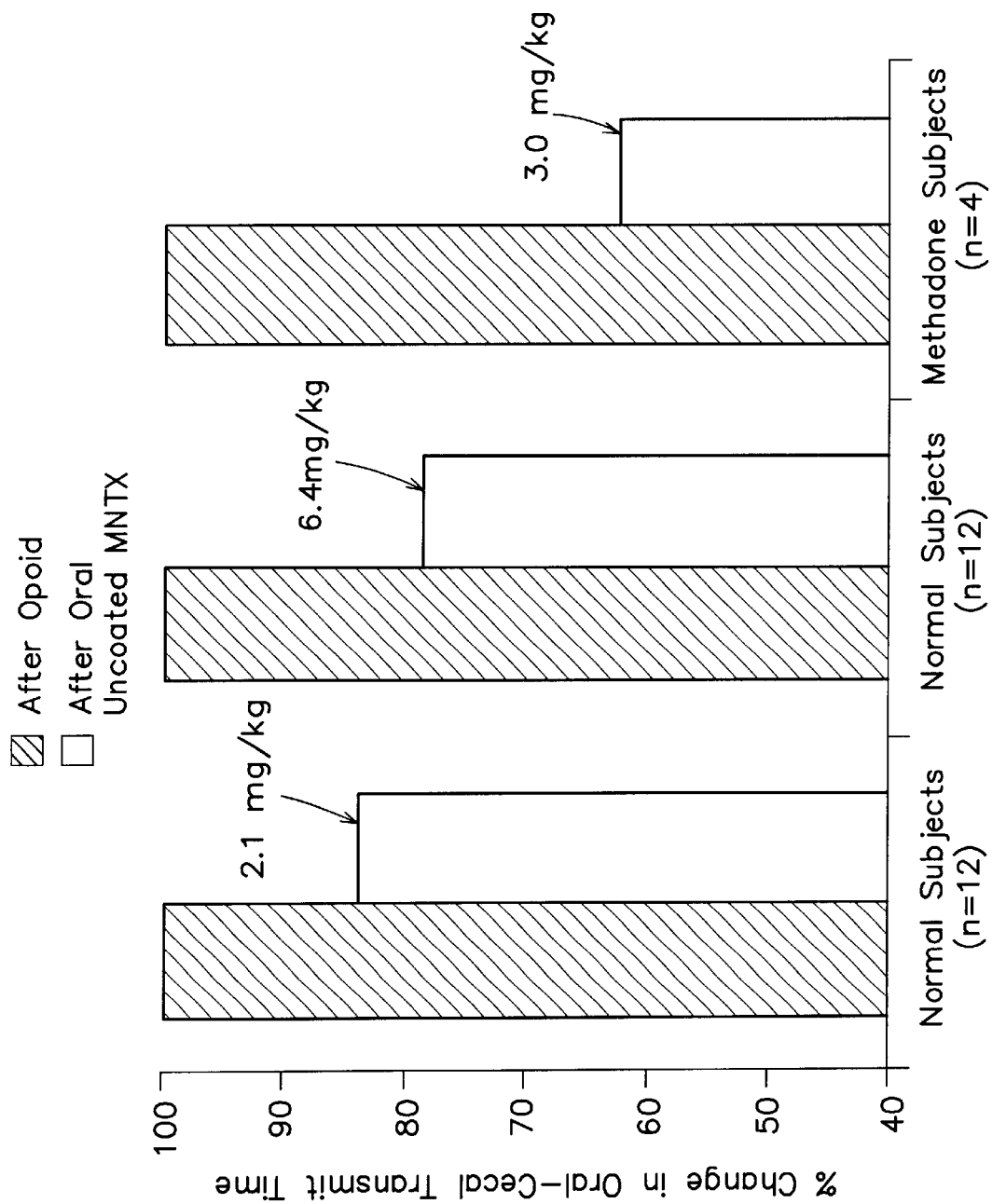
FIG. 5 is a comparison of oral-cecal transit times of normal volunteers and methadone maintenance subjects showing the increased responsiveness of chronic opioid patients to MNTX. At doses ranging from 2.1 mg/kg to 6.4 mg/kg, normal subjects experienced about a 15–20% reduction in oral-cecal transit time, while at a dose of 3.0 mg/kg, methadone subjects experienced a greater than 35% reduction in oral-cecal transit time.

Oral-cecal transit times are reported in FIG. 5. Transit time increased after morphine administration in all 12 subjects and methylnaltrexone prevented the morphine-induced delay in every subject. Morphine significantly increased oral-cecal transit time from a baseline level of 104.6±31.1 minutes (mean±SD) to 163.3±39.8 minutes p<0.01). Methylnaltrexone plus morphine did not increase transit time (106.3±39.8 minutes, not significant compared with baseline; p=0.56). Methylnaltrexone prevented 97% of morphine-induced changes in oral-cecal transit time (p<0.01 compared with morphine alone). There were not statistical differences in oral-cecal transit times between genders. Table 3 summarizes the results.

pation because of the change in the consistency of the stools. In this study, we observed a significant delay in oral-cecal transit time after intravenous morphine injection in human subjects and the delay was effectively antagonized by concomitant administration of methylnaltrexone. This result suggests that methylnaltrexone can reverse morphine-induced peripherally mediated effects on the gastrointestinal tract.

In the United States, approximately 500,000 patients die of cancer annually. Opioid pain medication is used in the terminal phase of care for over 50% of these patients, and constipation, a significant clinical problem, affects 40–50% (approximately 125,000) of patients with metastatic malignancy who receive opioid pain medications (Schug, et al., *J. Pain & Symptom Management,* 7:259–266 (1992); Wingo, et al., *Ca: A Cancer J. for Clin.,* 45:8–30 (1995)). A significant number of hospice patients receiving chronic opioids for pain would rather endure their pain than face the severe incapacitating constipation that opioids cause.

Results described herein demonstrate that chronic methadone subjects are very sensitive to intravenous methylnaltrexone compared to normal opioid naive subjects in a previous trial, who received 0.45 mg/kg methylnaltrexone without any laxation response (Yuan et al., *Clin. Pharmacol Ther.,* 59:469–475 (1996)). Comparison of the results of Example 4 with Examples 1–3 demonstrates the increased responsiveness of chronic opioid patients to the effects of methylnaltrexone. Lower doses of methylnaltrexone provide constipation relief to these patients comparable to that observed in normal patients administered higher doses of methylnaltrexone. Thus, patients having increased sensitiv-

TABLE 3

Pharmacokinetic parameters for 0.45 mg/kg intravenous methylnaltrexone in 12 subjects

| Subject No. | $C_{max}$(ng/ml) | AUC (ng/ml · hr) | $V_d\beta$ (L/kg) | $t_{1/2}\beta$(min) | CL (L/hr) | $F_u$ (%) |
|---|---|---|---|---|---|---|
| 1 | 3059 | 747 | 84.7 | 112.5 | 45.2 | 39.5 |
| 2 | 3119 | 677 | 82.4 | 106.3 | 46.5 | 40.4 |
| 3 | 4033 | 742 | 76.4 | 95.8 | 47.8 | 35.1 |
| 4 | 2640 | 658 | 87.7 | 87.5 | 60.1 | 34.0 |
| 5 | 2111 | 549 | 107.3 | 124.6 | 51.7 | 33.8 |
| 6 | 4309 | 694 | 166.9 | 162.6 | 61.6 | 36.5 |
| 7 | 1921 | 595 | 140.7 | 203.1 | 41.6 | 43.5 |
| 8 | 2418 | 637 | 246.9 | 238.1 | 62.2 | 26.6 |
| 9 | 5471 | 588 | 96.2 | 84.9 | 68.1 | 49.6 |
| 10 | 4076 | 1013 | 44.3 | 93.5 | 28.4 | 73.4 |
| 11 | 3443 | 634 | 139.2 | 114.2 | 73.2 | 44.4 |
| 12 | 2993 | 587 | 108.7 | 151.8 | 43.0 | 46.0 |
| Mean ± SD | 3299.4 ± 122.6 | 676.8 ± 122.6 | 115.1 ± 53.1 | 131.2 ± 48.7 | 52.5 ± 12.8 | 41.9 ± 11.8 |

$C_{max}$ Peak free plasma concentration, AUC, area under the plasm a concentration-time curve from 0 to 6 hours;
$V_d\beta$ T apparent volume of distribution during β phase (does not account for plasma protein binding);
$t_{1/2}\beta$, terminal half-life; CL, total body clearance;
$F_u$ percentage of does excreted unchanged in urine from 0 to 3 hours Discussion Humans do not appreciably de-methylate methylnaltrexone. Results from a phase I trial with eight normal volunteers showed that doses of methylnaltrexone up to 0.32 mg/kg did not cause side effects; doses of 0.64 to 1.25 mg/kg were associated with transient orthostatic hypotension (Foss et al., unpublished data, 1993).

The effect of opioids on gastrointestinal motility and transit is appreciated as a clinical phenomenon. However, the mechanism of the opioid constipating action is not fully understood. The major factors responsible include the delay of gastric emptying and changes in the motility and transit in the small intestine and the colon. Increased intestinal absorption may also contribute to morphine-induced constiity to methylnaltrexone, such as chronic methadone users or cancer patients receiving chronic opioids, can benefit from very low doses of methylnaltrexone to manage their opioid induced constipation. This invention can substantially improve the quality of life for terminally ill patients and others chronically using opioids.

The preceding description and Examples are intended to be illustrative. Those skilled in the art to which the invention pertains will appreciate that alterations and changes in the described protocols may be practiced without departing from the meaning, spirit, and scope of this invention. Therefore, the foregoing description should be read consistent with and as support to the following claims, which are to have their fullest and fair scope.

What is claimed is:

1. A method of preventing or treating an opioid-induced side effect in a chronic opioid patient, the method comprising administering a quaternary derivative of noroxymorphone in an amount sufficient to prevent or treat the side effect in the patient, wherein said amount is insufficient to treat the side effect in a patient to whom opioids have not been chronically administered and wherein said amount is such that peak plasma concentrations do not exceed 100 ng/ml.

2. The method of claim 1 wherein the quaternary derivative is methylnaltrexone.

3. The method of claim 2 wherein the side effect to be prevented or treated is constipation.

4. The method of claim 2 wherein the side effect is selected from the group consisting of dysphoria, pruritus, and urinary retention.

5. The method of claim 2 wherein the methylnaltrexone is enterically coated.

6. The method of claim 2 wherein the methylnaltrexone is administered in a form that is not enterically coated.

7. The method of claim 6 wherein the methylnaltrexone is administered orally.

8. The method of claim 2 wherein the methylnaltrexone is administered at a dosage of about 0.001 to about 5 mg/kg body weight.

9. The method of claim 2 wherein the methylnaltrexone is administered at a dose of less than about 3 mg/kg body weight.

10. The method of claim 2 wherein the methylnaltrexone is administered at a dose of less than about 1 mg/kg body weight.

11. The method of claim 2 wherein the methylnaltrexone is administered at a dose of less than about 0.1 mg/kg body weight.

12. The method of claim 2 wherein the peak plasma concentrations do not exceed 50 ng/ml.

13. The method of claim 2 wherein the peak plasma concentrations do not exceed 20 ng/ml.

14. The method of claim 2 wherein the peak plasma concentrations do not exceed 10 ng/ml.

15. The method of claim 2 wherein the methylnaltrexone is administered orally.

16. The method of claim 15 wherein the peak plasma concentrations do not exceed 50 ng/ml.

17. The method of claim 15 therein the peak plasma concentrations do not exceed 26 ng/ml.

18. The method of claim 15 wherein the peak plasma concentrations do not exceed 20 ng/ml.

19. The method of claim 15 wherein the peak plasma concentrations do not exceed 10 ng/ml.

20. The method of claim 2 wherein the methylnaltrexone is administered orally in a form that is enterically coated.

21. The method of claim 1 wherein the side effect to be prevented or treated is constipation.

22. The method of claim 1 wherein the side effect is selected from the group consisting of dysphoria, pruritus, and urinary retention.

23. The method of claim 1, wherein the opioid and the quaternary derivative of noroxymorphone are combined in an oral dose.

24. The method of claim 23 wherein the quaternary derivative is enterically coated.

25. The method of claim 1 wherein the quaternary derivative is administered orally in a form that is not enterically coated.

26. The method of claim 1 wherein the quaternary derivative is administered orally.

27. The method of claim 26 wherein the quaternary derivative is administered orally in a form that is enterically coated.

28. The method of claim 1 wherein the peak plasma concentrations do not exceed 50 ng/ml.

29. The method of claim 1 wherein the peak plasma concentrations do not exceed 20 ng/ml.

30. The method of claim 1 wherein the peak plasma concentrations do not exceed 10 ng/ml.

31. A method of preventing or treating opioid-induced constipation, the method comprising:

determining how long the patient has been administered opioids;

selecting a dose of a quaternary derivative of noroxymorphone based on the length of time the patient has been administered opioids, wherein the dose selected for a chronic opioid patient is at least 10% lower than the dose selected for a patient not chronically administered opioids, and wherein the dose is administered in an amount such that peak plasma concentrations do not exceed 100 ng/ml; and administering the selected dose of the quaternary derivative of noroxymorphone to the patient.

32. The method of claim 31 wherein the dose selected for a patient chronically administered opioids is at least 20% lower than the dose selected for a patient not chronically administered opioids.

33. The method of claim 31 wherein the dose selected for a patient chronically administered opioids is at least 30% lower than the dose selected for a patient not chronically administered opioids.

34. The method of claim 31 wherein the dose selected for a patient chronically administered opioids is at least 50% lower than the dose selected for a patient not chronically administered opioids.

35. The method of claim 31 wherein the dose selected for a patient chronically administered opioids is at least 70% lower than the dose selected for a patient not chronically administered opioids.

36. A method of preventing or reducing constipation in a chronic opioid patient, the method comprising administering a quaternary derivative of noroxymorphone in an amount sufficient to prevent or reduce the constipation in the patient, wherein said amount is not sufficient to reduce the constipation in a patient to whom opioids have not been chronically administered, and wherein said amount is administered in an amount such that peak plasma concentrations do not exceed 100 ng/ml.

37. A method of preventing or reducing urinary retention in a chronic opioid patient, the method comprising administering a quaternary derivative of noroxymorphone in an amount sufficient to prevent or reduce the urinary retention in the patient, where said amount is not sufficient to reduce the urinary retention in a patient to whom opioids have not been chronically administered, and wherein said amount is administered in an amount such that peak plasma concentrations do not exceed 100 ng/ml.

38. A method of preventing or reducing dysphoria in a chronic opioid patient, the method comprising administering a quaternary derivative or noroxymorphane in an amount sufficient to prevent or reduce the dysphoria in the patient, wherein said amount is not sufficient to reduce the dysphoria in a patient to whom opiods have not been chronically administered, and wherein said amount is administered in an amount such that peak plasma concentrations do not exceed 100 ng/ml.

39. A method of preventing or reducing pruritus in a chronic opioid patient, the method comprising administering a quaternary derivative or noroxymorphane in an amount sufficient to prevent or reduce the dysphoria in the patient, wherein said amount is not sufficient to reduce the pruritus in a patient to whom opiods have not been chronically administered, and wherein said amount is administered in an amount such that peak plasma concentrations do not exceed 100 ng/ml.

40. The method of any of claims 31, 36, 37, 38, or 39 wherein the peak plasma concentrations do not exceed 50 ng/ml.

41. The method of claim 40 wherein the peak plasma concentrations do not exceed 20 ng/ml.

42. The method of claim 40 wherein the peak plasma concentrations do not exceed 10 ng/ml.

43. The method of claim 31 or 36 wherein the peak plasma concentrations do not exceed 26 ng/ml.

* * * * *